United States Patent [19]

Yamazaki et al.

[11] Patent Number: 4,661,342

[45] Date of Patent: Apr. 28, 1987

[54] ORAL COMPOSITIONS COMPRISING HYDROXAMIC ACIDS AND SALTS THEREOF

[75] Inventors: Yoji Yamazaki, Hiratsuki; Toshiyuki Okada; Tsuneo Miyahara, both of Kanagawa, all of Japan

[73] Assignee: Lion Corporation, Tokyo, Japan

[21] Appl. No.: 800,164

[22] Filed: Nov. 20, 1985

[30] Foreign Application Priority Data

Nov. 20, 1984 [JP] Japan .................................. 59-245810

[51] Int. Cl.$^4$ .......................... A61K 31/19; A61K 7/22
[52] U.S. Cl. ...................................... 424/54; 514/575; 514/835
[58] Field of Search .................... 514/575, 835; 424/54

[56] References Cited

U.S. PATENT DOCUMENTS

| | | | |
|---|---|---|---|
| 3,427,381 | 2/1969 | Kirkland | 424/54 |
| 3,632,764 | 1/1972 | Wakeman et al. | 514/497 |
| 4,022,880 | 5/1977 | Vinson et al. | 424/55 |
| 4,093,711 | 6/1978 | Blackburne et al. | 424/54 |
| 4,291,045 | 9/1981 | Mackay et al. | 424/48 |

FOREIGN PATENT DOCUMENTS 52-21325  2/1977  Japan ..................................... 424/54
1093548  12/1967  United Kingdom ................ 514/575

OTHER PUBLICATIONS

Chem. Abst. 74:125092r, (1971)—Hase.
Chem. Abst. 77:92870z, (1972)—Noelser et al.
Chem. Abst. 87:63358q, (1977)—Wang et al.
Chem. Abst. 87:113115f, (1977)—Misato et al.

Primary Examiner—Douglas W. Robinson
Attorney, Agent, or Firm—Birch, Stewart, Kolasch & Birch

[57] ABSTRACT

There is provided an oral composition containing a hydroxamic acid represented by the formula $R-CH_2-CO-NHOH$ (where R is an alkyl group or alkoxyphenyl group) or a salt thereof such as 2-(4-butoxyphenyl)acetohydroxamic acid, 2-(4-methoxyphenyl)acetohydroxamic acid, caprylohydroxamic acid, or laurohydroxamic acid. The oral composition prevents Streptococcus mutans from colonizing in the oral cavity and is effective in preventing dental caries and also in preventing and remedying periodontal disease.

14 Claims, No Drawings

ORAL COMPOSITIONS COMPRISING HYDROXAMIC ACIDS AND SALTS THEREOF

BACKGROUND OF THE INVENTION

The present invention relates to an oral composition which prevents *Streptococcus mutans* from colonizing in the oral cavity and is effective in preventing dental caries and also in preventing and remedying periodontal disease.

Among oral bacterial *Streptococcus mutans* has long attracted attention because it causes dental caries. This bacterium produces a glucosyltransferase that synthesizes viscous polysaccharides such as dextran and mutan from sucrose. These polysaccharides form dental plaque in which the bacterial flora of *Streptococcus mutans* is present. This bacterium also produces acids from sugars and the acids stay in dental plaque to cause decalcification of enamel and tooth decay. In order to prevent tooth decay, it is important to avoid the colonization of *Streptococcus* mutans in the oral cavity. Presently, several methods have been proposed.

SUMMARY OF THE INVENTION

It is an object of the invention to provide an oral composition which can prevent dental caries and periodontal disease.

Most detailedly, the present inventors carried out a series of researches on this subject. As the result, it was found that a hydroxamic acid represented by formula (1) below:

R—CH$_2$—CO—NHOH  (1)

(where R is an alkyl group or alkoxyphenyl group) or a salt thereof prevents the colonization of *Streptococcus mutans* and an oral composition containing it is effective in the prevention of dental caries. It was also found that this compound is effective against gingivitis. Thus an oral composition incorporated with a hydroxamic acid represented by formula (1) or a salt thereof is effective not only in the prevention of dental caries but also in the prevention and remedy of periodontal disease.

In the meantime, it has been known that a hydroxamic acid represented by formula (1) above has antibacterial and antifungal properties and that 2-(4-butoxyphenyl)acetohydroxamic acid (Bufexamac) is a nonsteriodal anti-inflammatory drug for external use. In addition, there is disclosed in U.S. Pat. No. 3,427,381 an oral composition incorporated with benzohydroxamic acid

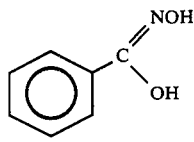

for the inhibition of dental plaque formation. Despite these previous findings, the present inventors are the first to discover that an oral composition incorporated with a hydroxamic acid represented by formula (1) or a salt thereof is effective in inhibiting the colonization of *Streptococcus mutans* and preventing dental caries. Moreover, the present inventors are the first to discover that an oral composition containing a compound of formula (1) is effective in the prevention and remedy of periodontal disease.

Therefore, this invention, provides an oral composition containing a hydroxamic acid represented by formula (1) below.

R—CH$_2$—CO—NHOH  (1)

(where R is an alkyl group or alkoxyphenyl group) or a salt thereof.

The above and other objects, features and advantages of the invention is apparent from the following description.

DETAILED DESCRIPTION OF THE INVENTION

The oral composition of this invention is available in the form of toothpaste, toothpowder, liquid dentifrice, mouthwash, gargle tablet, gingiva massage cream, chewing gum, or the like. It contains as an effective ingredient one or more kinds of hydroxamic acid represented by formula (1) below.

R—CH$_2$—CO—NHOH  (1)

(where R is an alkyl group or alkoxyphenyl group) and salts thereof.

Preferred examples of the hydroxamic acid represented by formula (1) include those compounds in which R is an alkyl group of carbon number 5 to 17, particularly 7 to 13, or an alkoxyphenyl group having an alkoxy group of carbon number 1 to 8, particularly 1 to 4. In the case of a compound where R is an alkoxyphenyl group, the alkoxyl group may be at ortho, meta, or para position; but preferably it should be at para position.

Preferred examples of such compounds include 2-(4-butoxyphenyl)acetohydroxamic acid, 2-(4-methoxyphenyl)-acetohydroxamic acid, caprylohydroxamic acid, and laurohydroxamic acid.

Salts of the hydroxamic acid include Na salt, K salt, Ca salt, Mg salt, and Al salt.

The content of a hydroxamic acid or a salt thereof represented by formula (1) above in the oral composition may be 0.005 to 5% by weight, preferably 0.02 to 1% by weight of the total weight of the composition.

The oral composition of this invention may further be incorporated with other commonly used ingredients which are selected according to the type of preparations.

For dentifrice, the oral composition may be incorporated with abrasive such as calcium secondary phosphate dihydrate, calcium secondary phosphate anhydride, calcium primary phosphate, calcium tertiary phosphate, calcium carbonate, calcium pyrophosphate, insoluble sodium metaphosphate, amorphous silica, crystalline silica, aluminosilicate, aluminum silicate, aluminum oxide, magnesium tertiary phosphate, magnesium carbonate, magnesium sulfate, titanium oxide, and resin.

For toothpaste, the oral composition may be incorporated with a binder such as sodium carboxymethylcellulose, methylcellulose, sodium carboxymethylhydroxyethylcellulose, hydroxyethylcellulose, sodium alginate, carrageenan, gum arabic, xanthane gum, tragacanth gum, calaya gum, polyvinyl alcohol, sodium polyacrylate, carboxyvinyl polymer, and polyvinyl pyrrolidone, and a humectant such as polyethylene glycol, ethylene glycol, sorbitol, glycerin, propylene glycol, 1,3-butylene glycol, xylit, maltit, and lactit.

The oral composition of this invention may be incorporated further with one kind or more of anionic, nonionic, cationic, and amphoteric surface active agents. Examples of the anionic surface active agents include sodium lauryl sulfate, sodium myristyl sulfate, and other water-soluble salts of alkyl sulfates having an alkyl group of carbon number 8 to 18; sodium coconutmonoglyceride sulfonate and other water-soluble higher acid monoglyceride sulfonates derived from a higher fatty acid having 10 to 18 carbon atoms; sodium salts of α-olefin sulfonate, paraffin sulfonate, and N-methyl-N-palmitoyltauride; sodium N-lauroyl sarcosinate; and sodium N-lauroyl-β-alanine. Examples of the nonionic surface active agents include lauroyl diethanolamide and other fatty acid alkanolamides; sucrose monolaurate, sucrose dilaurate, and other sucrose fatty acid esters; polyoxyethylene sorbitan fatty acid ester, polyoxyethylene fatty acid ester, polyoxyethylene hardened castor oil derivative, lactose fatty acid ester, lactitol fatty acid ester, maltitol fatty acid ester, and polyoxyethylene-polyoxypropylene block copolymer.

The oral composition of this invention may be incorporated further with an essential oil such as peppermint oil and spearmint oil; a flavoring component such as l-menthol, carvone, eugenol, and anethole; a sweetener such as saccharin sodium, stevioside, neohesperidyldihydrochalcone, glycyrrhizin, perillartine, and p-methoxycinnamic aldehyde; and a preservative.

In preparation of dentifrice, the blending amount of abrasive is preferably in the range of 1–99%, particularly 10–70% by weight of the composition. The blending amount of binder is preferably in the range of 0–5%, particularly 0.1–5% by weight of the composition. The blending amount of humectant is preferably in the range of 10–80%, particularly 30–60% by weight of the composition. The blending amount of surface active agent is preferably in the range of 0.1–5%, particularly 0.5–2% of the composition. The blending amount of sweetener is preferably 0.01–5%, particularly 0.05–2% by weight of the composition. The blending amount of flavor is preferably in the range of 0.1–5%, particularly 0.5–2% by weight of the composition.

The pH of the oral composition in liquid or paste type may preferably be in the range of 5–10.

The oral composition may further contain other effective ingredients in an effective amount including destranase, protease, lysozyme, lytic enzyme, mutanase, sorbic acid, alexidine, β-glycyrrhetinic acid, hinokiol, chlorhexidine, alkylglycine, alkyldiaminoethylglycine hydrochloride, allantoin, ε-aminocaproic acid, tranexamic acid, sodium monofluorophosphate, sodium fluoride, stannous fluoride, azuren, vitamin E, water-soluble primary and secondary phosphate, cetylpyridinium chloride and other quaternary ammonium compounds, sodium chloride, crude drug extracts.

For other types of formulation than mentioned above, proper ingredients can be incorporated in the usual way.

Being incorporated with hydroxamic acid represented by formula (1) or a salt thereof, the oral composition of this invention inhibits the colonization of *Streptococcus mutans* in the oral cavity and is effective in preventing dental caries and also effective in preventing and remedying periodontal disease.

The invention is now described with reference to the following examples, although the invention is not limited to these examples. "Percent (%)" in the formulations of the examples denotes "% by weight".

EXAMPLE 1

Dental plaque was artificially formed in a buffer solution (pH 6.8) containing 1% of sucrose, 0.01% of preservative ($NaN_3$), heat-sterilized cells of *Streptococcus mutans* (strain 6715), a predetermined amount of Bufexamac or laurohydroxamic acid, and exoenzymes (containing glucosyltransferase) produced by *Streptococcus mutans* (strain 6715). After reaction at 37° C. for 16 hours, the resulting dental plaque was washed twice with water and dispersed in the same amount of water, followed by the application of ultrasonic for about 20 seconds. To determine the amount of dental plaque formed, the suspension of dental plaque was examined for absorbance (turbidity) at a wavelength of 550 nm. The results are shown in Table 1.

TABLE 1

| Hydroxamic acid | Concn. (%) | Amount of dental plaque* |
|---|---|---|
| Bufexamac | 0.1 | 0.03 |
|  | 0.01 | 0.63 |
| Laurohydroxamic acid | 0.1 | 0.19 |
|  | 0.01 | 0.12 |
| Control | — | 0.69 |

*$OD_{550}$

EXAMPLE 2

ODU rats (7 weeks of age) were fed with a powder diet for 2 months so that dental plaque accumulated on the anterior teeth in the lower jaw to cause gingivitis experimentally. The rats, arranged in groups each consisting of five heads, were given the drug on the right and left of the gingiva of the anterior teeth in the lower jaw, twice a day for 20 days. On the day before the application of the drug and on the 20th day after the application of the drug, the area of inflammation was measured under a stereoscopic microscope to quantify the cure of gingivitis. The results are shown in Table 2. The drug was prepared by blending 0.5% of Bufexamac with a hydrophilic base. The hydrophilic base alone was used for control. The cure (%) of gingivitis was calculated from the following formula.

Cure (%) of gingivitis $= (A - B)/A \times 100$ where
A: Area of inflammation measured first
B: Area of inflammation measured last

TABLE 2

| Drug used | Cure of gingivitis |
|---|---|
| Control (base alone) | 18.0% |
| Base + 0.5% Bufexamac | 28.7%* |

*Significant at the 1% level by T-test.

EXAMPLE 3

Toothpaste

| | |
|---|---|
| Aluminum hydroxide | 45.0% |
| Gelling silica | 2.0 |
| Sorbit | 25.0 |
| Sodium carboxymethylcellulose | 1.0 |
| Sucrose monopalmitate | 1.0 |
| Sodium lauryl sulfate | 1.5 |
| Sodium saccharin | 0.2 |

-continued

| | |
|---|---|
| Ethanol | 0.1 |
| Sodium benzoate | 0.1 |
| 2-(4-butoxyphenyl)acetohydroxamic acid | 0.2 |
| Flavor | 1.0 |
| Water | Balance |
| | 100.0% |

EXAMPLE 4

Toothpaste

| | |
|---|---|
| Precipitated silica | 25.0% |
| Sorbit | 25.0 |
| Glycerin | 25.0 |
| Polyvinyl pyrrolidone | 1.0 |
| Lauroyl polyglycerin ester | 1.0 |
| Polyoxyethylene (60 mol) sorbitan monolaurate | 0.5 |
| Sodium saccharin | 0.2 |
| Ethyl parahydroxybenzoate | 0.1 |
| Chlorhexidine hydrochloride | 0.1 |
| Laurohydroxamic acid | 0.05 |
| Caprylohydroxamic acid | 0.05 |
| Flavor | 1.0 |
| Water | Balance |
| | 100.0% |

EXAMPLE 5

Toothpaste

| | |
|---|---|
| Calcium secondary phosphate dihydrate | 20.0% |
| Calcium secondary phosphate anhydride | 20.0 |
| Gelling silica | 2.0 |
| Sorbit | 20.0 |
| Sodium carboxymethylcellulose | 1.0 |
| Lauryl diethanolamide | 1.0 |
| Sodium lauryl sulfate | 1.5 |
| Lauroyl sarcosinate | 0.3 |
| Sodium saccharin | 0.1 |
| Ethyl parahydroxybenzoate | 0.1 |
| 2-(4-butoxyphenyl)acetohydroxamic acid | 0.1 |
| Magnesium phosphate | 1.0 |
| Sodium monofluorophosphate | 0.76 |
| Flavor | 0.8 |
| Water | Balance |
| | 100.0% |

EXAMPLE 6

Oral Paste

| | |
|---|---|
| Cetanol | 10.0% |
| Squalane | 20.0 |
| Abrasive precipitated silica | 5.0 |
| Polyoxyethylene (40 mol) hardened castor oil | 0.1 |
| Sorbitan monooleate | 1.0 |
| Glycyrrhetinic acid | 0.1 |
| Sodium saccharin | 0.6 |
| Flavor | 0.6 |
| 2-(4-butoxyphenyl)acetohydroxamic acid | 0.3 |
| Laurohydroxamic acid | 0.1 |
| Water | Balance |
| | 100.0% |

EXAMPLE 7

Oral Paste

| | |
|---|---|
| Liquid paraffin | 15.0% |
| Cetanol | 10.0 |

-continued

| | |
|---|---|
| Glycerin | 20.0 |
| Sorbitan monopalmitate | 0.6 |
| Polyoxyethylene (40 mol) sorbitan monostearate | 5.0 |
| Chlorhexidine gluconate | 0.1 |
| Flavor | 0.5 |
| 2-(4-butoxyphenyl)acetohydroxamic acid | 0.3 |
| Water | Balance |
| | 100.0% |

EXAMPLE 8

Mouthwash

| | |
|---|---|
| Sorbit | 10.0% |
| Ethanol | 5.0 |
| Polyoxyethylene (60 mol) hardened castor oil | 0.1 |
| Sucrose monopalmitate | 0.2 |
| Sodium saccharin | 0.2 |
| Flavor | 0.6 |
| 2-(4-butoxyphenyl)acetohydroxamic acid | 0.2 |
| Water | Balance |
| | 100.0% |

EXAMPLE 9

Oral troche

| | |
|---|---|
| Lactose | 99.0% |
| Chlorhexidine gluconate | 0.05 |
| Polyoxyethylene (60 mol) monostearate | 0.2 |
| 2-(4-butoxyphenyl)acetohydroxamic acid | 0.2 |
| Laurohydroxamic acid | 0.2 |
| Stevia extract | 0.2 |
| Flavor | 0.01 |
| Hydroxyethyl cellulose | Balance |
| | 100.0% |

What is claimed is:

1. An oral composition which inhibits the colonization of *Streptococcus mutans* in the oral cavity and is effective in preventing dental caries and periodontal disease comprising
a therapeutically effective amount of a hydroxamic acid represented by the following formula (1)

$$R-CH_2-CO-NHOH$$

(where R is an alkoxyphenyl group) or a salt thereof, and
at least one ingredient selected from the group consisting of abrasives, binders, humectants, surface active agents and flavors.

2. The oral composition of claim 1, wherein the hydroxamic acid represented by formula (1) is 2-(4-butoxyphenyl)acetohydroxamic acid or 2-(4-methoxyphenyl)-acetohydroxamic acid.

3. The oral composition of claim 1, wherein the amount of the hydroxamic acid or a salt thereof represented by formula (1) is 0.005 to 5% by weight of the composition.

4. The oral composition of claim 1, wherein the said oral composition is in a form selected from the group consisting of toothpaste, toothpowder, liquid dentifrice, mouthwash, gargle tablet, gingiva massage cream and chewing gum.

5. The oral composition of claim 1, wherein the hydroxamic acid represented by formula (1) is 2-(4-butoxyphenyl)-acetohydroxamic acid.

6. The oral composition of claim 4, wherein the hydroxamic acid represented by formula (1) is 2-(4-butoxyphenyl)-acetohydroxamic acid.

7. The oral composition of claim 6, wherein said oral composition is a toothpaste.

8. The oral composition of claim 4, wherein the amount of hydroxamic acid or salt thereof represented by formula (1) is 0.005 to 5% by weight of the composition.

9. The oral composition of claim 6, wherein the amount of the hydroxamic acid or salt thereof represented by formula (1) is 0.005 to 5% by weight of the composition.

10. The oral composition of claim 7, wherein the amount of the hydroxamic acid or salt thereof represented by formula (1) is 0.005 to 5% by weight of the composition.

11. A process for inhibiting colonization of *Streptococcus mutans* in the oral cavity and for preventing dental caries and periodontal disease comprising applying the composition of claim 1, to said oral cavity.

12. A process for inhibiting colonization of *Streptococcus mutans* in the oral cavity and for preventing dental caries and periodontal disease comprising applying the composition of claim 4, to said oral cavity.

13. A process for inhibiting colonization of *Streptococcus mutans* in the oral cavity and for preventing dental caries and periodontal disease comprising applying the composition of claim 6, to said oral cavity.

14. A process for inhibiting colonization of *Streptococcus mutans* in the oral cavity and for preventing dental caries and periodontal disease comprising applying the composition of claim 7, to said oral cavity.

* * * * *